US012677769B2

(12) United States Patent
Frederick et al.

(10) Patent No.: US 12,677,769 B2
(45) Date of Patent: Jul. 14, 2026

(54) POLLINATION CAGE AND POLLINATION METHOD

(71) Applicant: Aardevo B.V., Nagele (NL)

(72) Inventors: Curtis Frederick, Kampen (NL);
Ruben Hendrik Muilwijk, Harderwijk (NL)

(73) Assignee: Aardevo B.V., Nagele (NL)

( * ) Notice: Subject to any disclaimer, the term of this patent is extended or adjusted under 35 U.S.C. 154(b) by 276 days.

(21) Appl. No.: 18/318,353

(22) Filed: May 16, 2023

(65) Prior Publication Data

US 2023/0371451 A1     Nov. 23, 2023

(30) Foreign Application Priority Data

May 20, 2022     (GB) ...................................... 2207418

(51) Int. Cl.
| | |
|---|---|
| *A01H 1/02* | (2006.01) |
| *A01G 13/23* | (2025.01) |
| *A01G 22/25* | (2018.01) |

(52) U.S. Cl.
CPC ............. *A01H 1/027* (2021.01); *A01G 13/23* (2025.01); *A01G 22/25* (2018.02)

(58) Field of Classification Search
CPC ........ A01H 1/027; A01G 22/25; A01G 13/23; A01G 13/24; A01G 13/262; A01K 47/00; A01K 47/02; A01K 47/04; A01K 47/06; A01K 55/00
See application file for complete search history.

(56) References Cited

U.S. PATENT DOCUMENTS

| | | | | |
|---|---|---|---|---|
| 676,201 | A | * | 6/1901 | Patric ................... A01G 13/262 |
| | | | | 126/59.5 |
| 4,665,646 | A | * | 5/1987 | Anderson .............. A01G 13/24 |
| | | | | 47/21.1 |
| 2009/0223120 | A1 | * | 9/2009 | Astner ................. A01G 13/262 |
| | | | | 47/32.1 |
| 2009/0277083 | A1 | * | 11/2009 | Barnes ................... A01G 13/24 |
| | | | | 47/46 |
| 2016/0353677 | A1 | * | 12/2016 | Toye ...................... A01G 13/27 |
| 2017/0238475 | A1 | * | 8/2017 | Van Pelt ................. A01G 9/28 |
| 2018/0014514 | A1 | * | 1/2018 | Freneaux ............... A01K 47/06 |
| 2020/0149869 | A1 | * | 5/2020 | Egwu ..................... G01B 11/02 |

(Continued)

FOREIGN PATENT DOCUMENTS

| | | | | | |
|---|---|---|---|---|---|
| CH | | 415159 | A | * 6/1966 | .......... A01G 3/0231 |
| CN | | 204907363 | U | 12/2015 | |
| CN | | 106508822 | A | * 3/2017 | ............. A01K 67/30 |

(Continued)

OTHER PUBLICATIONS

Combined Search and Examination Report regarding GB2207418. 1, dated Nov. 10, 2022.

*Primary Examiner* — Katelyn T Truong

(74) *Attorney, Agent, or Firm* — Harness, Dickey & Pierce, P.L.C.

(57)     ABSTRACT

Disclosed herein is a pollination cage for the field pollination of a ridge planted crop, the pollination cage comprising: a plurality of frames; and one more nets supported by the plurality of frames; wherein: the frames and one or more nets define at least one enclosed region for containing pollinating insects; and each frame comprises a notched structure for placing on ridged ground.

21 Claims, 6 Drawing Sheets

(56)        References Cited

U.S. PATENT DOCUMENTS

2020/0337257  A1 *  10/2020  Kumar ................. G01N 27/121
2023/0279686  A1 *   9/2023  Condra ................. A01K 47/00
                                                  52/101

FOREIGN PATENT DOCUMENTS

CN          108450323  A      8/2018
EP            3238529  A1 *  11/2017   ............ A01G 22/10
JP         2004113009  A      4/2004
JP            3921663  B2 *   5/2007
KR        20130022961  A  *   3/2013   ........... A01G 9/1438

* cited by examiner

POLLINATION CAGE AND POLLINATION METHOD

CROSS REFERENCE TO RELATED APPLICATIONS

This application claims the benefit of priority from Great Britain Patent Application No. GB2207418.1, filed on May 20, 2022, the entire disclosure of which is incorporated herein by reference.

FIELD OF THE INVENTION

The present invention relates to the field pollination of ridge planted crops. Embodiments provide a new pollination cage with a number of advantages over known techniques.

BACKGROUND

It is well known that the self-pollination of crops by insects increases yield. Pollination is also required for cross-breeding different varieties of a crop.

There is a general need to improve on known crop pollination techniques.

SUMMARY OF THE INVENTION

Aspects of the invention are set out in the appended independent claims. Optional aspects are set out in the dependent claims.

DESCRIPTION OF THE DRAWINGS

The present invention will now be described, by way of non-limitative example only, with reference to the following figures, in which.

DETAILED DESCRIPTION

A known technique for a pollinating a crop is by hand pollination in a greenhouse. However, this is an expensive process due to the labour costs and the greenhouse mainte-nance costs.

A known alternative to pollination in a greenhouse is field pollination. Field pollination is the pollination of a crop that has already been planted in a field. In field pollination, a pollination cage is constructed over a crop. Pollinating insects are enclosed within the pollination cage and pollinate the covered crop.

Field pollination may be substantially less expensive than pollination in a greenhouse. However, a number of problems may be identified with known pollination cages for field pollination that result in them being unsuitable for use on a large scale. For example, known pollination cages are not suitable for use with machinery. Processes such as crop planting, crop spraying and crop harvesting all need to be performed by hand. Known pollination cages are also not designed for use with a crop that is planted in ridges. Known pollination cages may also have a circular footprint on the ground. Using a plurality of such pollination cages will not entirely cover the ground of a field. Known pollination cages are also not easily adaptable for use in different configura-tions.

Embodiments provide a new pollination cage for the field pollination of a crop that solves at least some of the above-identified problems.

Embodiments provide a modular pollination cage. The pollination cage according to embodiments comprises one or more nets that provide an enclosed region, or a plurality of separate enclosed sub-regions, within which pollinating insects are retained. The one or more nets are supported by a plurality of frames. The frames may be easily adapted to generate and change the enclosed sub-regions. The frames may also be easily moved to allow easy construction and adaption of the pollination cage. The frames are also designed for use with ridge planted crops.

Pollination cages according to embodiments are described in more detail below.

Figure 1A:
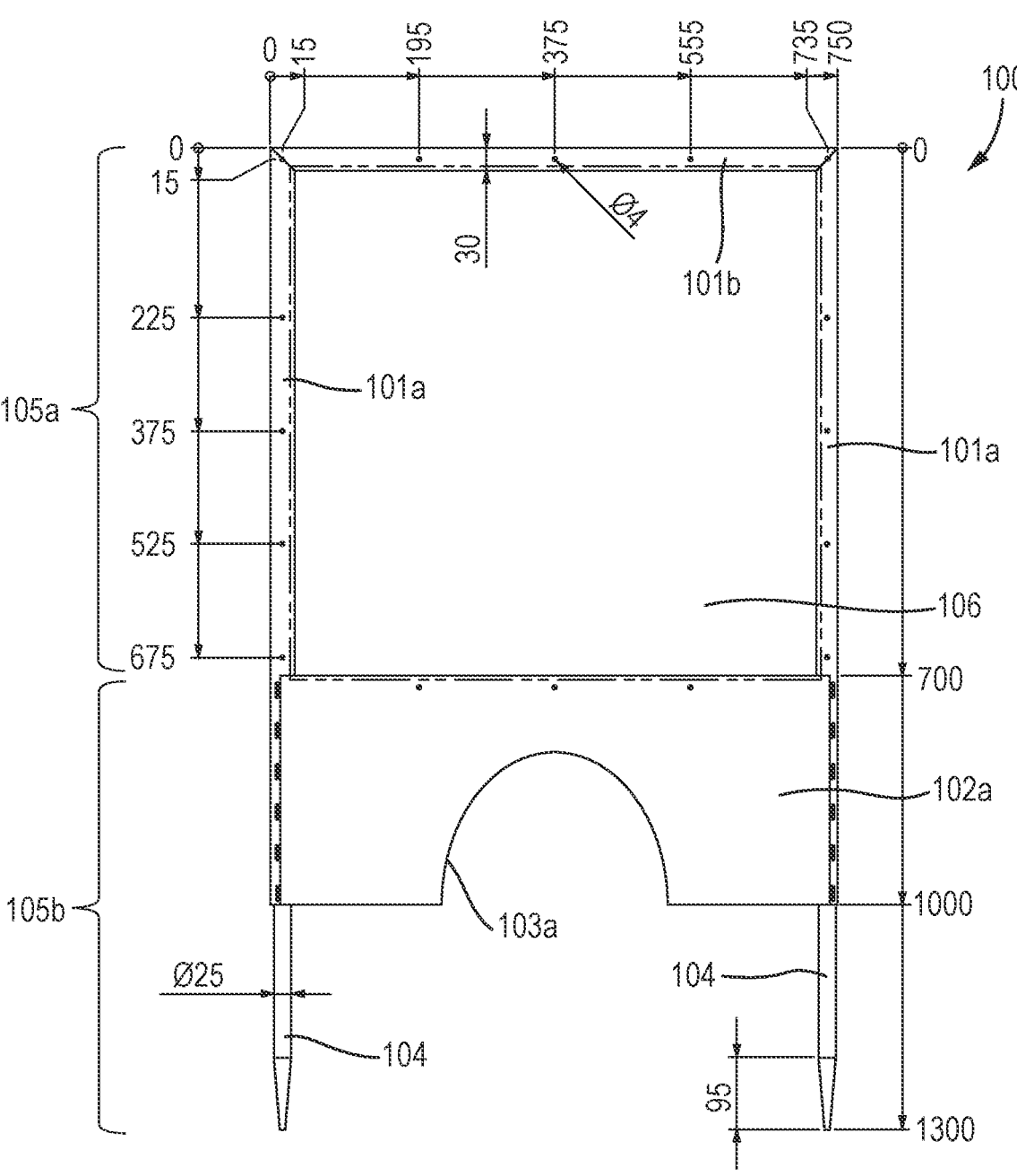
FIGS. 1A to 1C schematically show a first implementation of a frame according an embodiment.
Figure 1B:
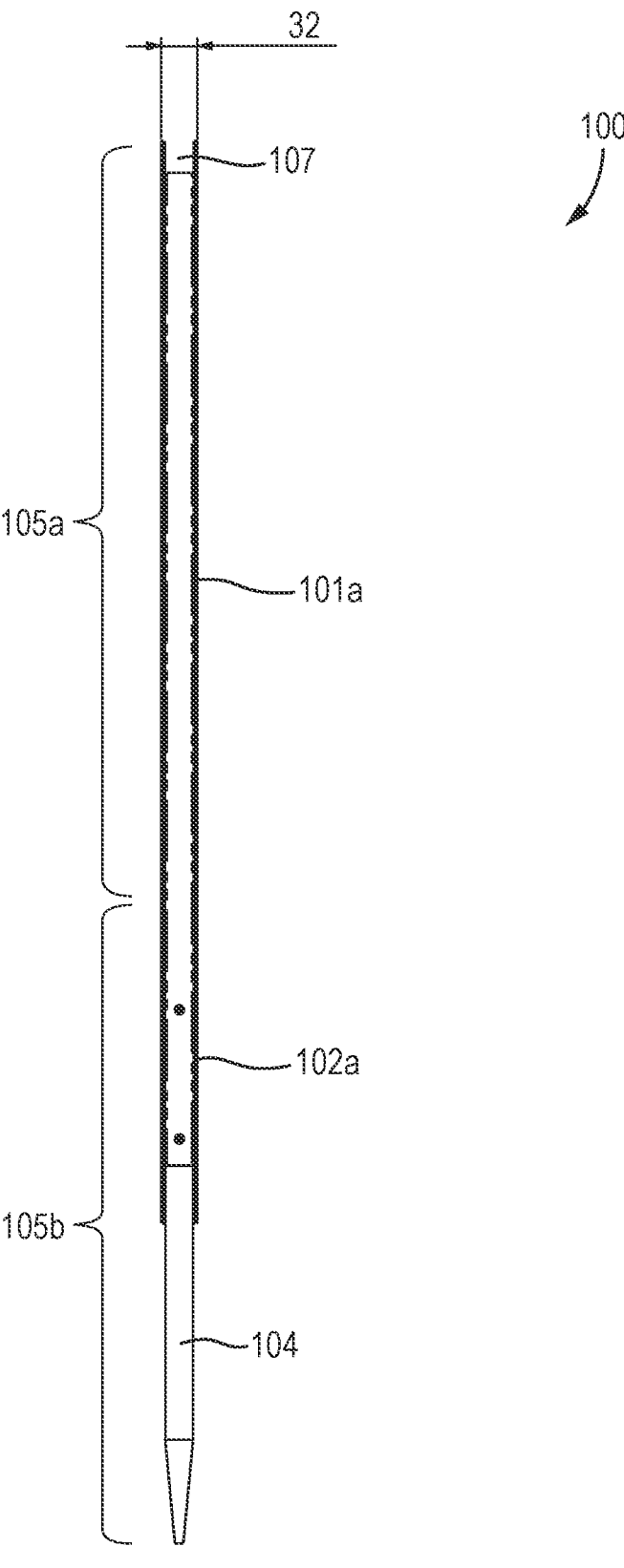
Figure 1C:
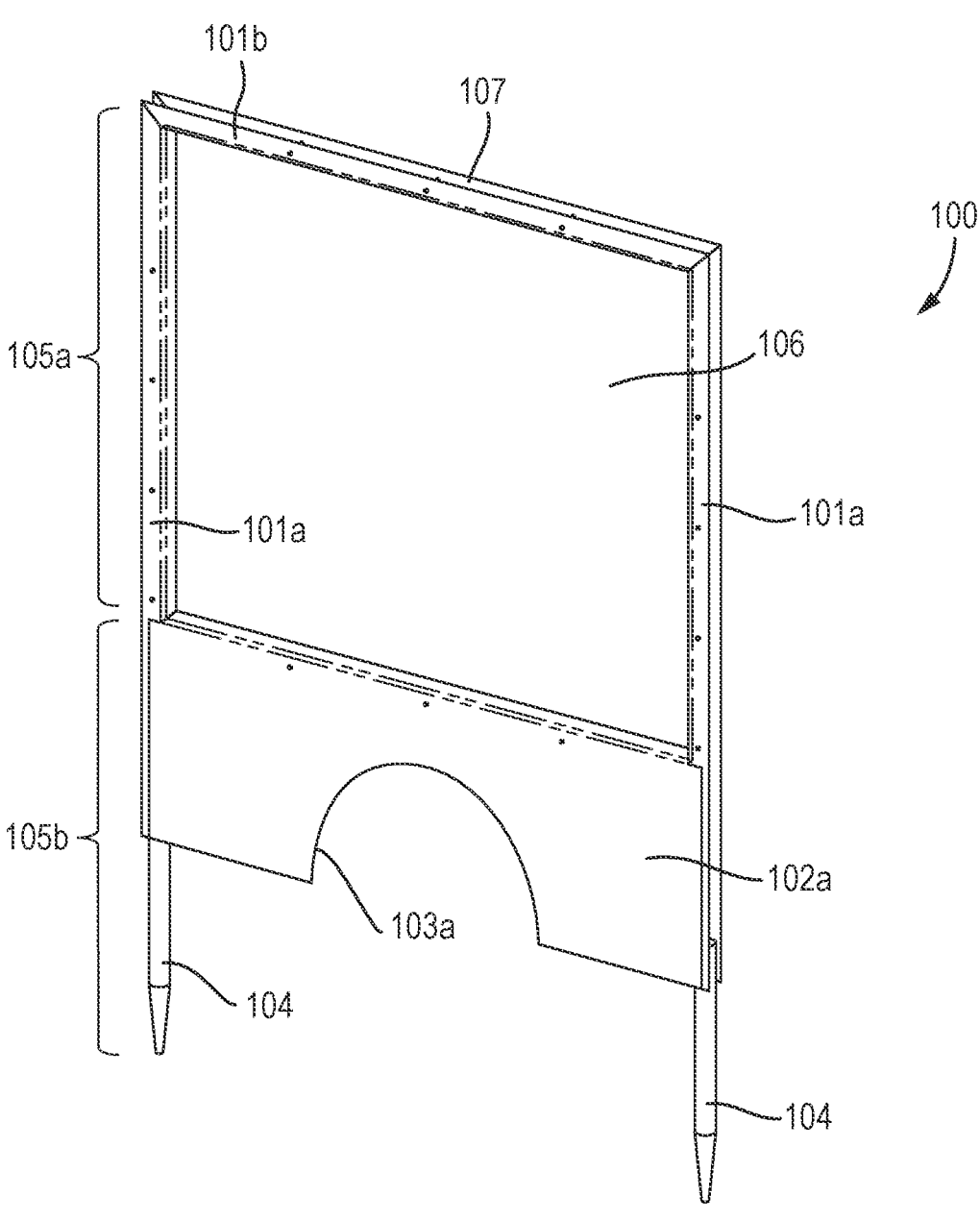

FIGS. 1A to 1C show a first implementation of a frame 100 according an embodiment.

The frame 100 may be a substantially planar structure with a lower part 105$b$ and an upper part 105$a$.

The lower part 105$b$ of the frame may comprise a base structure 102$a$ and one or more spikes 104. The lower part of the base structure 102$a$ may comprise a notch 103$a$. The base structure 102$a$ may also be referred to as a notched structure or a board.

There may be a downward extending spike 104 at each of two opposing ends of the base structure 102$a$. Each spike 104 may be inserted into the ground so as to secure the frame 100 in a field. When secured in a field, the frame may protrude substantially vertically from substantially horizon-tal ground.

The notch 103$a$ in the base structure 102$a$ may be arranged so that, when the frame 100 is secured in ridged ground, the notch 103$a$ receives a ridge of the ground. The lower surface of the base structure 102$a$ may thereby be substantially flush with the surface of the ridged ground without being substantially inserted into the ground. Accord-ingly, there is no gap between the lower part of the base structure 102$a$ and the ridged ground that insects may pass through.

The shape of the notch 103$a$ is preferably substantially the same shape as the shape of the ridge in the ground. The shape of the notch 103$a$ may be substantially semi-circular, or substantially semi-oval. If the base structure 102$a$ did not comprise a notch 103$a$, the frame 100 would not be suitable for use with ridged ground because there would be a gap between the base structure 102$a$ and the ground that insects could pass through.

The upper part 105$a$ of the frame may comprise a net support 101$a,b$. A first part 101$a$ of the net support 101$a,b$ may comprise rods, or bars, that extend from the base structure 102$a$ in an opposite direction to the spikes 104. A second part 101$b$ of the net support 101$a,b$ may comprise a rod, or crossbar, that connects the opposite ends of the first part 101$a$ from the ends at the base structure 102$a$.

Each first part 101$a$ of the net support 101$a,b$ may be part of a single rod that also comprises the spike 104 that extends from the other side of base structure 102$a$ to the first part 101$a$. The first part 101$a$ may thereby be integrally formed with the spike 104. An end of the base structure may be welded, such as chain welded, to the single rod.

The net support 101a,b and base structure 102a may define a frame opening 106. The frame opening 106 is a hole through the frame. The frame opening 106 may be arranged to support a net.

As shown in FIGS. 1B and 1C, the frame 100 may comprise a channel 107 on its outward facing side and upper surfaces. The channel 107 may be formed in an outward facing side surface of each first part 101a of the net support 101a,b, an outward facing side surface of the second part 101b of the net support 101a,b, and in the outward facing side surfaces of the base structure 102a. The channel 107 may be arranged to receive a tie along its length. The tie may be, for example, a rope, a cord, an elastic bungee or any other type of fastener.

As described in more detail later with reference to FIG. 2, when a net is provided over the frame 100, a tie that is received in the channel may secure the net to the frame 100. The contact between the tie and the side and base surfaces of the channel 107 may provide three seals, with each seal preventing insects travelling between the outward facing surfaces of the frame 100 and the net.

Possible approximate dimensions of the first implementation of the frame 100 are:

Length of each spike 104=300 mm

Height of the base structure 102a=300 mm

Length of the base structure 102a=750 mm

Depth of the base structure 102a=32 mm

Length of each first part 101a of the net support 101a, b=700 mm

Diameter of each first part 101a of the net support 101a,b=25 mm

Length of each second part 101a of the net support 101a,b=750 mm

Diameter of each second part 101a of the net support 101a,b=30 mm

Figure 1D:
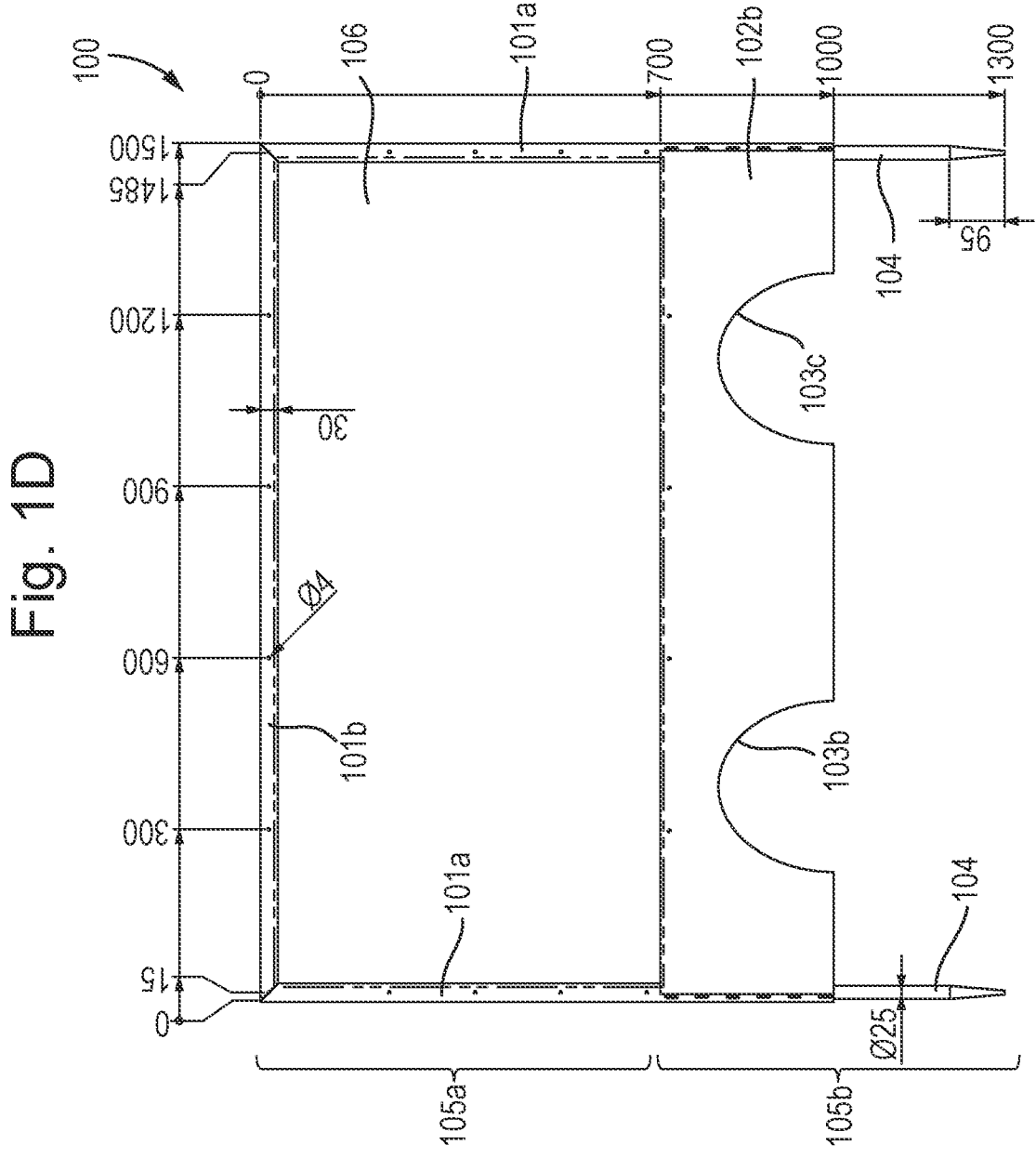
FIG. 1D schematically shows a second implementation of a frame according an embodiment.

FIG. 1D shows a second implementation of a frame 100 according to an embodiment.

In the second implementation of the frame 100, the base structure 102b of the frame 100 comprises two notches 103b,c instead of only a single notch 103a. To accommodate the two notches 103b,c, the base structure 102b in the second implementation may be longer than the base structure 102a of the first implementation. Similarly, the second part 101b of the net support 101a,b may also be longer. For example, the length of the base structure 102a, and the second part 101b of the net support 101a,b, may both be increased to 1500 mm. In all other respects, the second implementation of the frame 100 may be substantially the same as the first implementation of the frame 100.

In the second implementation of the frame 100, the two notches 103b,c allow the frame to span over two parallel ridges when the frame 100 is inserted into ridged ground. Wider pollination cages may therefore be constructed with the second implementation of the frame 100 than the first second implementation of the frame 100.

Figure 2:
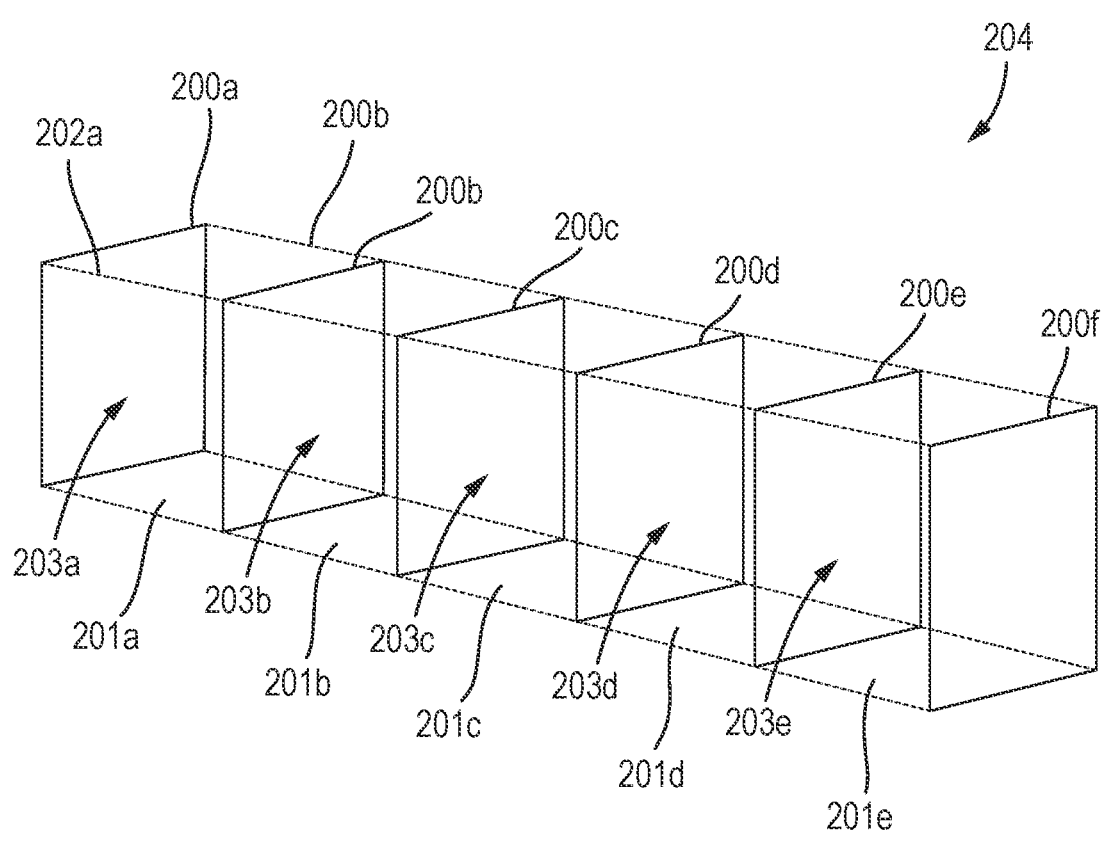
FIG. 2 schematically shows a pollination cage according to an embodiment.

FIG. 2 schematically shows a pollination cage according to an embodiment.

The pollination cage 204 comprises a plurality of frames 200a-f. All of the frames 200a-f may be substantially identical to each other. Each frame 200a-f may be either one of the above-described first or second implementations of a frame 100. It should be noted that FIG. 2 shows the relative locations of the frames 200a-f without showing the specific details of each frame, such as the presence of at least one notch 103a, b, c.

Frames 200a and 200f are end frames of the pollination cage 204. Each end frame 200a,f, may support a net that entirely covers the frame opening 106 of the end frame 200a,f. The mesh of the net is chosen so that the insects that are used for pollinating the crop are unable to pass through it. The end frames 200a,f thereby provide covered end surfaces of the pollination cage 204.

Frames 200b to 200e are intermediate frames of the pollination cage 204. The intermediate frames 200b-e are all located between the end frames 200a,f.

The end frames 200a,f and intermediate frames 200b-e may be aligned with each other with the planes of all of the frames 200a-f parallel to each other. The frames 200a-f may be located along one or more linear ridges of the ground.

The frames provide a support structure for an outer net that extends over all of the frames 200a-f. In FIG. 2, net corners 202a,b are shown for the outer net. The mesh of the outer net is chosen so that the insects that are used for pollinating the crop are unable to pass through it.

To secure the outer net to each frame 200a-f, the outer net may be provided over each frame when there is no tie in the channel 107 of each frame 200a-f. A tie may then be inserted into the channel 107 of each frame 200a-f so that a tie secures the net to each frame 200a-f. Each tie may be, for example, a rope, a cord, an elastic bungee or any other type of fastener. For each frame 200a-f, one end of each tie may be attached to an outer surface of an end of the base structure 102a,b, and an opposite end of each tie may be attached to an outer surface of an opposite end of the base structure 102a,b.

When the outer net is secured over the frames 200a-f, a pollination cage 204 is formed with an entire enclosed internal region of the pollination cage 204 defined by the outer net, the end frames 200a,f (that each have their frame openings 106 covered by a net) and the ground. Pollinating insects may thereby be retained within the pollination cage 204.

As shown in FIG. 2, the pollination cage 204 may a linear single structure. The intermediate frames 200b-e separate the ground covered by the pollination cage 204 into a plurality of separate plots 201a-e. Each intermediate frame 200b-e may be used either with a net that covers its frame opening 106, or without such a net. The net used to cover a frame opening 106 may have the same mesh as the outer net so that pollinating insects are unable to pass through it.

When each intermediate frame 200b-e comprises a net that covers its frame opening 106, then the internal region of the pollination cage 204 is divided into a plurality of enclosed sub-regions 203a-e. Each enclosed sub-region 203a-e is bounded by two adjacent frames, that each comprise a net that covers their frame opening 106, part of the outer net and one of the plots 201a-e of ground. For example, the enclosed sub-region 203a is defined by the end frame 200a, the intermediate frame 200b, part of the outer net and the plot 201a.

The volume of each enclosed sub-region may be varied by removing one or more nets of the intermediate frames 200b-e. By removing the net, pollinating insects are able to freely move between the different enclosed sub-regions. For example, if the frame opening 106 of the intermediate frame 200b is removed, but all of the other intermediate frames 200c-e have nets covering their frame openings 106, then enclosed sub-regions 203a and 203b are combined into a single enclosed sub-region. The combined enclosed sub-region is still separate from the other enclosed sub-regions 203c-e.

The entire enclosed internal region of the pollination cage 204 may be re-configured to be a single enclosed region, or a plurality of separate enclosed sub-regions within a common physical structure, by removing and adding nets of the intermediate frames 200*b-e*. The plots 201*a-e* covered by each enclosed sub-region may also be varied in dependence on which ones of the intermediate frames 200*b-e* have their frame openings covered by a net.

The height of the pollination cage 204 above the ground is substantially the height of each frame 200*a-f* above the ground. When a frame is secured in the ground by spikes 104, and the frame 100 is protruding substantially vertically from horizontal ground, the height of the frame is the height of the base structure 102*a* combined with the length of each first part 101*a* of the net support 101*a,b*. The height of each frame above the ground, and thereby the height of the pollination cage 204, may be about 1000 mm.

The height of the pollination cage 204 above the ground is preferably arranged so that machinery, such a crop sprayer, may be used above the pollination cage. There may be legal requirements that restrict the height of a crop sprayer to being no more than 20 cm above the height of the crop. The height of the pollination cage may therefore need to be set within a range defined by the height of the crop in order for a crop sprayer to be used. Embodiments include using frames with different lengths of each first part 101*a* of the net support 101*a,b* so that the height of the pollination cage is set to being only slightly higher than the height of the crop.

Another advantage of the pollination cage 204 according to an embodiment is that the crop may be easily and quickly accessed. By removing one of more of the ties that attach the outer net to the frames 200*a-f,* the outer net may be partially slid back, or entirely removed. This allows the crop to be inspected. Depending on the circumstances, it may also be appropriate to remove the outer net when the crop is being sprayed. The use of the outer net may also only be required during the flowering period of the crop and so the outer net, and possibly also the frames 200*a-f,* may be removed at other times.

Figure 3:
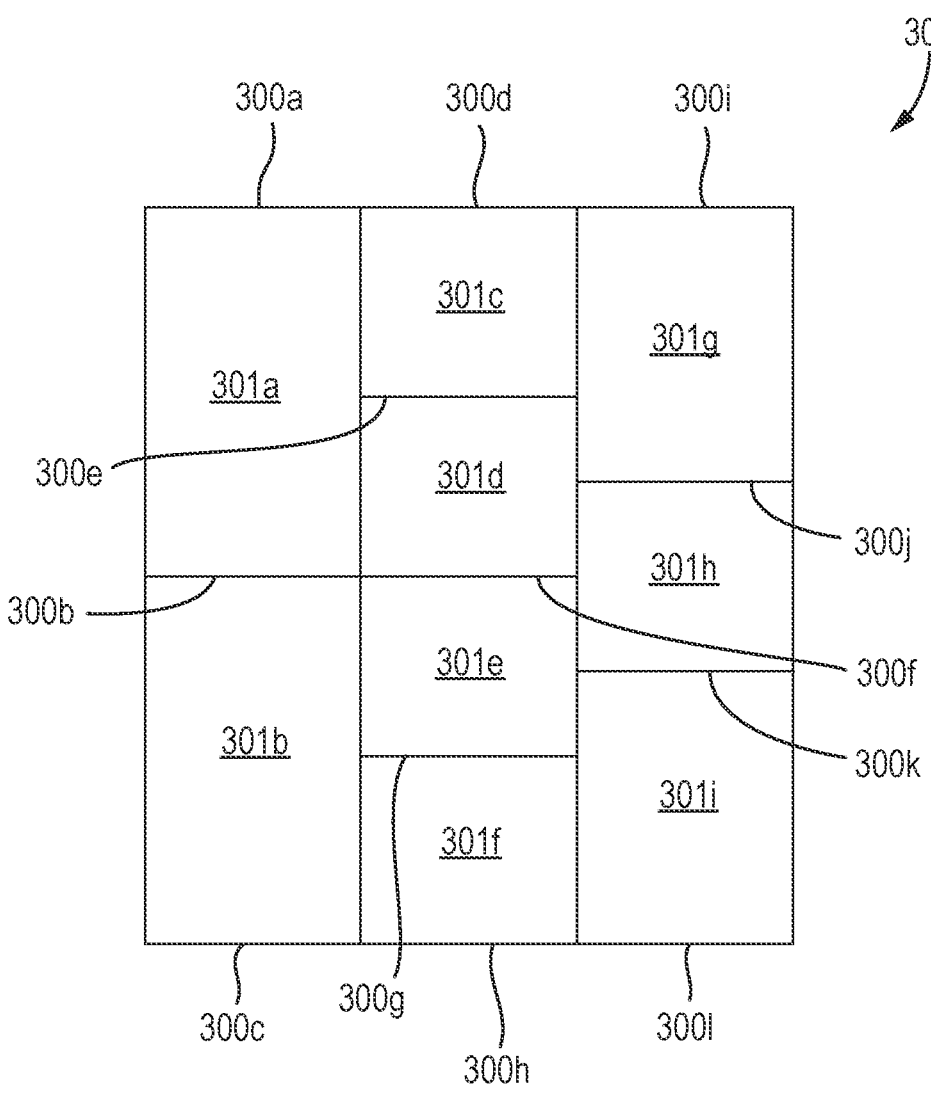
FIG. 3 schematically shows a pollination cage according to an embodiment in plan view.

FIG. 3 schematically shows another configuration of pollination cage 302 according to an embodiment in plan view.

The pollination cage 302 in FIG. 3 differs from that in FIG. 2 by the pollination cage 302 having enclosed sub-regions arranged in a plurality of abutting rows. The pollination cage 302 comprises end frames 300*a,c,d,h,i,l* and intermediate frames 300*b,e,f,g,j,k*. The shown intermediate frames 300*b,e,f,g,j,k* all have nets covering their frame openings so that the location of the intermediate frames 300*b,e,f,g,j,k* defines the location of the plots of ground 301*a-i* of respective enclosed sub-regions.

Although not shown in FIG. 3, the pollination cage 302 may comprise further intermediate frames that do not have their frame openings 106 covered by a net and so do not define a boundary of an enclosed sub-region. Each of the separate rows of the pollination cage 302 may be provided by a single row pollination cage 204 as shown in FIG. 2. Accordingly, the pollination cage 302 may be a plurality of neighbouring separate pollination cages 204.

The different sizes and locations of the plots of ground 301*a-i* of respective enclosed sub-regions demonstrate how the pollination cage 302 may be flexibly configured when deployed in a field. The pollination cage 302 may also be flexibly re-configured by adding or removing nets that cover the frame openings of the intermediate frames 300*b,e,f,g,j,k*.

The pollination cage 302 is modular with its overall size, and the shape of its footprint, defined by the locations of the frames. The overall size of the pollination cage 302 may be increased by using more frames and nets. The shape of the footprint of the pollination cage 302 may also be easily changed by moving the locations of the frames. The pollination cage 302 may entirely cover a rectangular field, and substantially cover most other shapes of field.

The pollination cages 204, 302 according to embodiments may provide a number of further advantages over known techniques.

The pollination cages 204, 302 according to embodiments are designed to be constructed in a field. This is substantially cheaper than greenhouse pollination techniques.

The pollination cages 204, 302 according to embodiments are designed for use with ridge planted crops. These may include potatoes, onions, carrots, chicory and other ridge planted crops.

The pollinating insect used in a pollination cage is selected based on the type of crop that is planted. The nets used are selected so that they are appropriate given the type of pollinating insect. For potatoes, the pollinating insect is a bee, such as a bumblebee. The mesh size of the nets used is therefore selected so that it is too small for bees to pass through. Onions and carrots may alternatively be pollinated by flies. For onions and carrots, the mesh size of the nets used is therefore selected so that it is too small for flies to pass through.

In a particularly preferred embodiment, the crop is potatoes and the pollinating insect is a bumblebee.

Embodiments include a number of modifications and variations to the techniques described above.

In particular, embodiments include a parallel arrangement of a plurality of the pollination cages 204 as shown in FIG. 2. There may be a footpath between adjacent pollination cages 204 so that all of the plots of ground may be easily accessed.

The base structure 102*a,b* of each frame is not restricted to comprising one or two notches 103*a,b,c*. The base structure 102*a,b* of each frame may comprise more than two notches so that each frame may extend over more than two ridges.

The above-described outer net may be a single net. Alternatively, the outer net may comprise two or more separate nets. In particular, each tie that secures the outer net to a frame may be similarly used to secure the ends of more than one net to the same frame.

In the above-described embodiments, the first part 101*a* and second part 101*b* of the net support 101*a,b* define a frame opening 106 with a rectangular cross-section. This may be a preferred implementation because it provides a large enclosed region for the pollinating insects. Embodiments also include the use of a net support that defines a frame opening 106 with a semi-circular cross-section. Such an implementation may facilitate the attachment and removal of the outer net.

Embodiments also include the net supports 101*a,b* being configured to receive other types of cover than nets. In particular, the net supports 101*a,b* may be configured to receive suitable covers for protecting the crop from frost, heavy rains etc.

Embodiments also include securing remote sensors to the pollination cages 204, 302. The sensors may be used, for example, to monitor the state of the crop being grown, the growing conditions of the crop, and/or the state of the pollination cages 204, 302.

The sensors may be secured to, or integrated with, parts of each frame 100. In particular, the pollination cages 204, 302 may be fitted with soil moisture sensors. The soil moisture sensors may be provided in the spikes 104. Other types of sensors that may be used include cameras for recording, and optionally measuring, the growth and/or flowering of the crop. Spectroscopic sensors may also be used to measure the properties, e.g. multi-spectral parameters, of the light. Light detection and ranging (LIDAR) sensors may be used to measure the growth of the crop and/or state of the pollination cage 204, 302. Movement sensors, such as accelerometers, may be used to detect any movement of the pollination cage 204, 302. If the state of the pollination cage 204, 302 changes, for example due to the pollination cage 204, 302 being damaged by adverse weather, the changed state of the pollination cage 204, 302 may be automatically detected. Positioning sensors, such as GPS sensors, may be used so that all of the obtained data by the sensors may be automatically recorded with the location of the measurement.

A communication system may be provided at the pollination cages 204, 302 that is configured to automatically transmit the obtained data by the sensors, by either wired or wireless communication, to a central system. At the central system, the obtained data may be automatically displayed so that human operators may remotely monitor the crop. The central system may automatically generate alerts when the obtained data indicates that there is a potential problem, or undesirable condition, with the crop and/or pollination cage 204, 302.

Embodiments also include using agronomic/cultivation technologies with the pollination cages 204, 302. In particular, heaters may be secured to the pollination cages 204, 302 for frost protection. The pollination cages 204, 302 may be configured so that fertilization and irrigation technologies may be used on the crop. For example, conduits may supply a drip feed of water or liquid chemicals to the crop in the pollination cages 204, 302.

Embodiments include the following numbered clauses:

1. A pollination cage for the field pollination of a ridge planted crop, the pollination cage comprising:
   a plurality of frames; and
   one more nets supported by the plurality of frames;
   wherein:
   the frames and one or more nets define at least one enclosed region for containing pollinating insects; and
   each frame comprises a notched structure for placing on ridged ground.
2. The pollination cage according to clause 1, wherein, for each frame:
   the notched structure substantially provides the lower part of the frame;
   the upper part of the frame is defined by one or more net supports that extend upwards from the lower part of the frame;
   the one or more net supports and notched structure define an opening through the frame; and
   the one or more net supports are arranged to support a frame opening net that covers the opening through the frame.
3. The pollination cage according to clause 1 or 2, wherein the opening has a square, rectangular or semi-circular cross-section.
4. The pollination cage according to clause 2 or 3, wherein, for each frame, at least one of the net supports comprises a channel on its outward facing surface for receiving a fastener for securing a net to the net support.
5. The pollination cage according to clause 4, wherein, when a fastener is received by the channel, the fastener and channel form a seal for pollinating insects.

6. The pollination cage according to any preceding clause, wherein the frames are substantially planar structures; and
   the frames are arranged substantially in parallel and inline with each other so that a linear tunnel is defined between the frames.
7. The pollination cage according to clause 6, wherein the pollination cage has a square or rectangular footprint on the ground.
8. The pollination cage according to clause 6 or 7, wherein, when the pollination cage is arranged on a crop that is planted in a linear row, the plane of each frame is orthogonal to the direction of the row.
9. The pollination cage according to any preceding clause, wherein each frame is configured so that each net that the frame is arranged to support is both removable from the frame and also re-securable to the frame.
10. The pollination cage according to any preceding clause, wherein the pollination cage is configured to cover a plurality of plots and to provide a separate enclosed region for each plot.
11. The pollination cage according to any of clauses 2 to 10, wherein the pollination cage comprises:
    two end frames at opposite ends of the pollination cage; and
    one or more intermediate frames that are located between the two end frames;
    wherein:
    each end frame comprises a frame opening net; and
    the number of separate enclosed plots with the pollination cage is reconfigurable in dependence on use of frame opening nets on the intermediate frames.
12. The pollination cage according to any preceding clause, wherein each net is arranged so that, when the pollinating insect is a bee, the pollinating insect is unable to pass through the net.
13. The pollination cage according to any preceding clause, wherein the pollination cage is arranged for use with a potato crop.
14. The pollination cage according to any preceding clause, wherein the notched structure of each frame comprises only one notch for receiving a ridge of the ridged ground.
15. The pollination cage according to any of clauses 1 to 13, wherein the notched structure of each frame comprises a plurality of notches for receiving respective plurality of ridges of the ridged ground.
16. The pollination cage according to any preceding clause, wherein, in use, the height of the frame above the ground is about 1000 mm.
17. The pollination cage according to any preceding clause, wherein each frame comprises one or more spikes for insertion into the ground.
18. The pollination cage according to any preceding clause, further comprising one or more sensors configured to monitor the state of a crop being grown in the pollination cage, the growing conditions of the crop, and/or the state of the pollination cage.
19. The pollination cage according to clause 18, when dependent on clause 17, wherein at least one spike comprises a soil moisture sensor.
20. The pollination cage according to clause 18 or 19, further comprising a communication system configured to automatically transmit obtained data by the sensors to a central system for remotely monitoring the crop.
21. A frame for use in a pollination cage according to any of clauses 1 to 20.

22. A method of reconfiguring the number of enclosed regions by a pollination cage for the field pollination of a ridge planted crop, the method comprising:

securing one or more frame opening nets to intermediate frames of the pollination cage; and/or removing one or more frame opening nets from intermediate frames of the pollination cage.

23. The method according to clause 22, further comprising increasing the footprint of the pollination cage by:

adding one or more frames to the pollination cage; and providing one or more nets that extend a region enclosed by the pollination cage to the one or more added frames.

24. The method according to clause 22 or 23, wherein the pollination cage is according to clause 11, or any clause dependent thereon.

25. A method of pollinating a crop, the method comprising:

constructing a pollination cage above a planted crop; and providing pollinating insects within the pollination cage; wherein the pollination cage is according to any of clauses 1 to 20.

26. The method according to clause 25, wherein the pollinating insects are bees.

27. The method according to clause 25 or 26, wherein the planted crop is a potato crop.

28. The method according to any of clauses 25 to 27, wherein the pollination type is cross and/or self pollination.

29. A method of tending to a planted crop, the method comprising:

constructing a pollination cage above a planted crop, wherein the pollination cage is according to any of clauses 1 to 20; and spraying the planted crop by a crop sprayer that moves over the constructed pollination cage.

30. A method comprising constructing a pollination cage, wherein the pollination cage is according to any of clauses 1 to 20.

31. The use of a pollination cage in a method for pollinating a crop, wherein the pollination cage is according to any of clauses 1 to 20.

The accompanying drawings are provided for purposes of illustration only, and the dimensions, positions, order, and relative sizes reflected in the drawings attached hereto may vary. The detailed description will be better understood in conjunction with the accompanying drawings, with reference made in detail to embodiments of the present subject matter, examples of which are illustrated in the drawings. Each example is provided by way of explanation of the present subject matter, not limitation of the present subject matter. In fact, it will be apparent to those skilled in the art that various modifications and variations can be made in the present disclosure without departing from the scope of the present subject matter. Thus, it is intended that the present subject matter covers such modifications and variations as come within the scope of the appended claims and their equivalents.

In the foregoing description, it will be appreciated that the phrases "at least one", "one or more", and "and/or", as used herein, are open-ended expressions that are both conjunctive and disjunctive in operation. The term "a" or "an" entity, as used herein, refers to one or more of that entity. As such, the terms "a" (or "an"), "one or more" and "at least one" can be used interchangeably herein. All directional references (e.g., proximal, distal, upper, lower, upward, downward, left, right, lateral, longitudinal, front, back, top, bottom, above, below, vertical, horizontal, radial, axial, clockwise, counterclockwise, and/or the like) are used for identification purposes to aid the reader's understanding of the present disclosure, and/or serve to distinguish regions of the associated elements from one another, and do not limit the associated element, particularly as to the position, orientation, or use of this disclosure.

The invention claimed is:

1. A pollination cage for the field pollination of a ridge planted crop, the pollination cage comprising:

a plurality of frames; and one or more nets supported by the plurality of frames;

wherein the frames and one or more nets define at least one enclosed region for containing pollinating insects;

wherein each frame comprises a notched structure for placing on ridged ground, wherein the notched structure includes a board with a notch;

wherein the notched structure substantially provides the lower part of the frame and is configured such that, when the frame is placed on ridged ground, the ridge is received by the notch;

wherein the board has a lower surface for contacting flush against the ridged ground when the frame is placed on the ridged ground, the lower surface comprising flat regions for providing flush contact with flat parts of ridged ground, and the lower surface also comprising the notch for providing flush contact with the ridge in the ridged ground; and wherein over a third of the lower surface is provided by the flat regions.

2. The pollination cage according to claim 1, wherein, for each frame:

the upper part of the frame is defined by one or more net supports that extend upwards from the lower part of the frame;

the one or more net supports and notched structure define an opening through the frame; and the one or more net supports are arranged to support a frame opening net that covers the opening through the frame.

3. The pollination cage according to claim 1, wherein the opening has a square, rectangular or semi-circular cross-section;

wherein, for each frame, at least one of the net supports comprises a channel on its outward facing surface for receiving a fastener for securing a net to the net support; and wherein, when a fastener is received by the channel, the fastener and channel form a seal for pollinating insects.

4. The pollination cage according to claim 1, wherein:

the frames are substantially planar structures;

the frames are arranged substantially in parallel and inline with each other so that a linear tunnel is defined between the frames;

the pollination cage has a square or rectangular footprint on the ground;

and, when the pollination cage is arranged on a crop that is planted in a linear row, the plane of each frame is orthogonal to the direction of the row.

5. The pollination cage according to claim 1, wherein each frame is configured so that each net that the frame is arranged to support is both removable from the frame and also re-securable to the frame.

6. The pollination cage according to claim 1, wherein the pollination cage is configured to cover a plurality of plots and to provide a separate enclosed region for each plot.

11

7. The pollination cage according to claim 1, wherein, for each frame:

the upper part of the frame is defined by one or more net supports that extend upwards from the lower part of the frame;

the one or more net supports and notched structure define an opening through the frame; and the one or more net supports are arranged to support a frame opening net that covers the opening through the frame; and wherein the pollination cage further comprises:

two end frames at opposite ends of the pollination cage; and one or more intermediate frames that are located between the two end frames;

wherein each end frame comprises a frame opening net; and wherein the number of separate enclosed plots with the pollination cage is reconfigurable in dependence on use of frame opening nets on the intermediate frames.

8. The pollination cage according to claim 1, wherein each net is arranged so that, when the pollinating insect is a bee, the pollinating insect is unable to pass through the net.

9. The pollination cage according to claim 1, wherein the pollination cage is arranged for use with a potato crop.

10. The pollination cage according to claim 1, wherein the notched structure of each frame comprises only one notch for receiving a ridge of the ridged ground.

11. The pollination cage according to claim 1, wherein the notched structure of each frame comprises a plurality of notches for receiving respective plurality of ridges of the ridged ground.

12. The pollination cage according to claim 1, wherein, in use, the height of the frame above the ground is about 1000 mm.

13. The pollination cage according to claim 1, wherein each frame comprises one or more spikes for insertion into the ground.

14. The pollination cage according to claim 1, further comprising one or more sensors configured to monitor the state of a crop being grown in the pollination cage, the growing conditions of the crop, and/or the state of the pollination cage.

15. The pollination cage according to claim 1, wherein each frame comprises one or more spikes for insertion into the ground; and at least one spike comprises a soil moisture sensor.

16. The pollination cage according to claim 1, further comprising:

one or more sensors configured to monitor the state of a crop being grown in the pollination cage, the growing conditions of the crop, and/or the state of the pollination cage; and a communication system configured to automatically transmit obtained data by the sensors to a central system for remotely monitoring the crop.

17. The pollination cage according to claim 1, wherein at least a half of the lower surface is provided by the flat regions.

18. A method of reconfiguring the number of enclosed regions by a pollination cage for the field pollination of a ridge planted crop, the method comprising:

securing one or more frame opening nets to intermediate frames of the pollination cage;

and/or removing one or more frame opening nets from intermediate frames of the pollination cage;

wherein the pollination cage comprises:

a plurality of frames; and one more nets supported by the plurality of frames; and wherein the frames and one or more nets define at least one enclosed region for containing pollinating insects; and wherein each frame comprises a notched structure for placing on ridged ground, wherein the notched structure includes a board with a notch, wherein the board has a lower surface for contacting flush against the ridged ground when the frame is placed on the ridged ground; and wherein, for each frame:

the notched structure substantially provides the lower part of the frame;

the upper part of the frame is defined by one or more net supports that extend upwards from the lower part of the frame;

the one or more net supports and notched structure define an opening through the frame; and the one or more net supports are arranged to support a frame opening net that covers the opening through the frame; and wherein the pollination cage further comprises:

two end frames at opposite ends of the pollination cage; and one or more intermediate frames that are located between the two end frames;

wherein each end frame comprises a frame opening net; and wherein the number of separate enclosed plots with the pollination cage is reconfigurable in dependence on use of frame opening nets on the intermediate frames.

19. The method according to claim 18, further comprising increasing the footprint of the pollination cage by:

adding one or more frames to the pollination cage; and providing one or more nets that extend a region enclosed by the pollination cage to the one or more added frames.

20. A method of pollinating a crop, the method comprising:

constructing a pollination cage according to claim 1 above a planted crop; and providing pollinating insects within the pollination cage;

wherein the frames and one or more nets define at least one enclosed region for containing pollinating insects.

21. The method according to claim 20, wherein:

the pollinating insects are bees;

the planted crop is a potato crop; and the pollination type is cross and/or self pollination.

* * * * *